United States Patent
Fisher et al.

(10) Patent No.: US 6,753,358 B2
(45) Date of Patent: Jun. 22, 2004

(54) PHOTOCROSSLINKING OF DIETHYL FUMARATE/POLY(PROPYLENE FUMARATE) BIOMATERIALS

(75) Inventors: John P. Fisher, Houston, TX (US); Antonios G. Mikos, Houston, TX (US)

(73) Assignee: William Marsh Rice University, Houston, TX (US)

( * ) Notice: Subject to any disclaimer, the term of this patent is extended or adjusted under 35 U.S.C. 154(b) by 0 days.

(21) Appl. No.: 10/185,473

(22) Filed: Jun. 28, 2002

(65) Prior Publication Data

US 2003/0032733 A1 Feb. 13, 2003

Related U.S. Application Data

(60) Provisional application No. 60/335,242, filed on Oct. 31, 2001, and provisional application No. 60/301,575, filed on Jun. 28, 2001.

(51) Int. Cl.[7] .............................. C08F 2/50; C08F 22/00
(52) U.S. Cl. ..................... 522/18; 522/107; 525/444; 525/445; 521/18
(58) Field of Search ................. 522/18, 107; 525/444, 525/445; 521/50.5; 523/105

(56) References Cited

U.S. PATENT DOCUMENTS

| | | | | |
|---|---|---|---|---|
| 4,722,948 A | * | 2/1988 | Sanderson | 523/115 |
| 4,888,413 A | | 12/1989 | Domb | 528/282 |
| 5,512,600 A | | 4/1996 | Mikos et al. | 521/61 |
| 5,514,378 A | | 5/1996 | Mikos et al. | 424/425 |
| 5,522,895 A | | 6/1996 | Mikos | 623/16 |
| 5,527,864 A | | 6/1996 | Suggs et al. | 525/444 |
| 5,696,175 A | | 12/1997 | Mikos et al. | 521/61 |
| 5,733,951 A | * | 3/1998 | Yaszemski et al. | 523/116 |
| 6,072,022 A | | 6/2000 | O'Brien et al. | 528/295 |
| 6,124,373 A | * | 9/2000 | Peter et al. | 523/116 |
| 6,153,664 A | * | 11/2000 | Wise et al. | 523/115 |
| 6,283,997 B1 | | 9/2001 | Garg et al. | 623/16.11 |
| 6,306,821 B1 | | 10/2001 | Mikos et al. | 514/2 |
| 6,355,755 B1 | | 3/2002 | Peter et al. | 526/320 |
| 6,384,105 B1 | | 5/2002 | He et al. | 523/113 |
| 6,423,790 B1 | | 7/2002 | He et al. | 525/445 |
| 2002/0171178 A1 | * | 11/2002 | Dean et al. | 264/401 |

OTHER PUBLICATIONS

Alger, "Polymer Science Dictionary", 2nd ed., Chapman & Hall, New York, p. 374 (1997).*

* cited by examiner

Primary Examiner—D. R. Wilson
(74) Attorney, Agent, or Firm—Conley Rose, P.C.

(57) ABSTRACT

A polymer network formed by crosslinking poly(propylene fumarate) with a fumarate derivative. The fumarate derivative is one in which the PPF is soluble, is preferably an alkyl fumarate, and is more preferably selected from the group consisting of diethyl fumarate, dimethyl fumarate, methyl ethyl fumarate, diisopropyl fumarate, and dibutyl fumarate. The network can be formed by photo-crosslinking and can be porous. In some embodiments, the poly(propylene fumarate) and the fumarate derivative are each present in an amount effective to produce a polymeric network useful for in vivo applications. The network can be formed from an injectable, in situ crosslinkable composite formulation, or can be prefabricated from a crosslinkable composite formulation such as stereolithography, rapid prototyping, injection molding, and extrusion molding.

10 Claims, 12 Drawing Sheets

PHOTOCROSSLINKING OF DIETHYL FUMARATE/POLY(PROPYLENE FUMARATE) BIOMATERIALS

RELATED CASES

The present case claims the benefit of U.S. provisional applications Serial No. 60/335,242, filed Oct. 31, 2001, and entitled Photocrosslinking Characteristics and Mechanical Properties of Diethyl Fumarate/Poly (Propylene Fumarate) Biomaterials, and Serial No. 60/301,575, filed Jun. 28, 2001, and entitled Photocrosslinking of Diethyl Fumarate and Poly (Propylene Fumarate) for the Engineering of Bone Grafts, both of which are incorporated herein by reference.

STATEMENT REGARDING FEDERALLY SPONSORED RESEARCH OR DEVELOPMENT

This work was funded by the National Institutes of Health (R01-DE13740).

TECHNICAL FIELD OF THE INVENTION

This invention relates to a compound for replacing or reconstructing bone. More particularly, the present invention relates to compositions comprising poly(propylene fumarate) cross linked with diethyl fumarate and methods for making these compositions.

BACKGROUND OF THE INVENTION

In the field of tissue engineering, degradable biomaterials can serve as a scaffold to provide mechanical support and a matrix for the ingrowth of new tissue. As new tissue forms on the scaffold, the biomaterial degrades until it is entirely dissolved. The degradation products are eliminated through the body's natural pathways, such as metabolic processes.

One example of the use of such biomaterials is as a temporary bone replacement. It is often desired to replace or reconstruct all or a portion of a living bone, such as when a bone has been broken or has been resected as a result of a bone tumor. In these instances, the missing bone can be replaced with a mechanical device, such as a pin, plate or the like, or it can be replaced with an implant that is designed to more closely resemble the original bone itself. Often these implants comprise biodegradable polymeric compounds or parts made from such compounds. It is contemplated that bone tissue will grow back into the pores of the implant and will gradually replace the entire implant as the implant itself is gradually degraded in the in vivo environment. Thus it is desirable that such implants be biocompatible and non-toxic.

Poly(propylene fumarate) is one such polymer. Poly (propylene fumarate) (hereinafter "PPF") is an unsaturated linear polyester that degrades in the presence of water into propylene glycol and fumaric acid, degradation products that are easily cleared from the human body by normal metabolic processes. Because the fumarate double bonds in PPF are reactive and cross link at low temperatures, PPF has potential to be an effective in situ polymerizable biomaterial. The high mechanical strength of cured PPF matrices and their ability to be cross linked in situ makes them especially suitable for orthopedic applications, including bone cement, orthopaedic scaffolding for bone tissue regeneration, and drug delivery systems.

In particular, an injectable matrix is desired. A principle advantage of injectable biomaterials lies in their ability to completely fill the irregularly shaped bone defects that often arise clinically. Other advantages include their ease of use, allowance of minimally invasive surgical procedures, and ability to act as a carrier of cells or bioactive agents. The development of an injectable, in situ polymerizable biomaterial, however, requires the consideration of a number of material characteristics that are not often evaluated for other biomaterials, including uncured solution viscosity and heat evolution during curing. Hence, despite advances in the technology, there remains a need for an effective, injectable, in situ polymerizable biomaterial. The development of tissue engineered materials for the treatment of large bone defects would provide attractive alternatives to the autografts, allografts, non-degradable polymers, ceramics, and metals that are currently used in clinical settings.

PPF has been investigated as a bone graft/bone scaffolding material. PPF contains a repeating fumarate unit that is comprised of one carbon—carbon double bond and two ester groups. The carbon—carbon double bond allows the viscous PPF polymer to be crosslinked into a solid, while each ester group allows PPF to degrade, via ester hydrolysis, into biocompatible fragments [6]. Photocrosslinked PPF has been formed into scaffolds, shown to elicit a mild tissue response, and, when loaded with transforming growth factor beta 1 (TGF-β1), shown to promote the formation of bone in a rabbit cranial defect model [7–9]. A photocrosslinkable biomaterial such as this PPF-based system may be suitable both for treatments that prefer a prefabricated implant and treatments that prefer an injectable biomaterial that is cured by light, either during or after its injection.

At high PPF molecular weights, however, the polymer becomes quite viscous, inhibiting its handling properties and, by definition, markedly reduces its ability to flow. This viscous nature of PPF has repercussions for both injectable and prefabrication processes. Hence, it is desired to create a PPF system that possesses a significantly reduced viscosity, while still retaining the advantageous characteristics of fumarate-based biomaterials.

SUMMARY OF THE INVENTION

The present invention comprises new, injectable biodegradable polymer composites based on PPF cross linked with a fumarate derivative, and in particular with diethyl fumarate. According to the present invention, poly (propylene fumarate) (PPF), a viscous polyester synthesized from a fumarate precursor such as diethyl fumarate (DEF), is use as an engineered bone graft. More specifically, the photocrosslinking of PPF dissolved in a fumarate precursor such as DEF, using a photoinitiator such as bis(2,4,6-trimethylbenzoyl) phenylphosphine oxide (BAPO) and low levels of ultraviolet light exposure, is disclosed.

In order to investigate the various characteristics of the present fumarate polymers, a three-factor, 2×2×4 factorial design was applied to the composition, so that the effects of PPF number average molecular weight, BAPO initiator content, and DEF content upon photocrosslinking characteristics and mechanical properties could be studied.

It was discovered that for uncured DEF/PPF solution viscosity fell over three orders of magnitude as DEF content was increased from 0 to 75%. The exothermic photocrosslinking reaction releases low levels of heat, with no more than 160 J/g released from any formulation tested. As a result, the maximum photocrosslinking temperature remained below 47° C. for all samples. Sol fraction varied from 26 to 65%, with composites of high PPF molecular weight and high BAPO content containing the smallest sol fraction. Compressive mechanical properties were within the range of trabecular bone, with the strongest samples possessing an elastic modulus of 195.3±17.5 MPa and a fracture strength of 68.8±9.4 MPa. Finally, the results indicated that PPF crosslinking was facilitated at low DEF precursor concentrations, but hindered at higher precursor concentrations.

The invention comprises the compositions formed by dissolving PPF in a fumarate solvent, the polymeric networks formed by crosslinking those compositions, and to methods for making items comprised of the polymer networks. These novel DEF/PPF solutions may be preferred over pure PPF as the basis for an engineered bone graft as they: (1) exhibit reduced viscosity and thus are easily handled, (2) form polymer networks with compressive strengths at fracture that are suitable for consideration for trabecular bone replacement, and (3) may be readily fabricated into solids with a wide range of structures.

BRIEF DESCRIPTION OF THE FIGURES

For a more detailed understanding of the present invention, reference is made to the accompanying Figures, wherein.

DETAILED DESCRIPTION OF THE PREFERRED EMBODIMENTS

Figure 1:
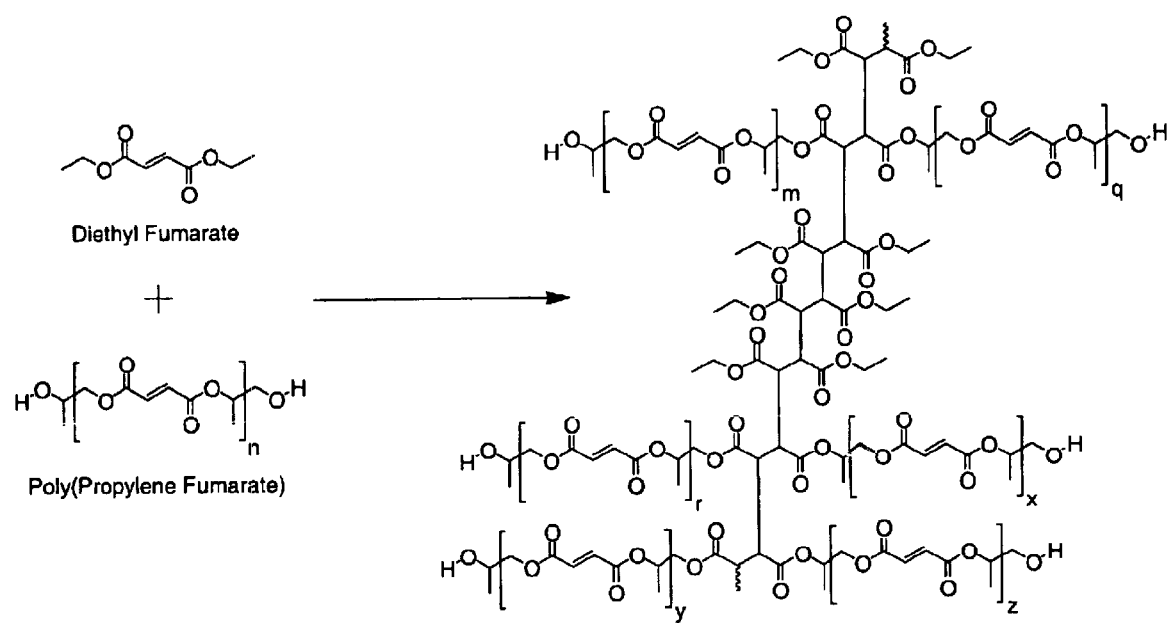
FIG. 1 is a schematic diagram depicting polyaddition reactions that occur between poly(propylene fumarate) and diethyl fumarate.

The present invention comprises a class of biomaterials that are formed by the photocrosslinking of the PPF polymer dissolved in a fumarate derivative such as an alkyl fumarate. An example of a suitable fumarate derivative is (DEF), a diester precursor from which PPF can be synthesized. DEF contains the crosslinkable carbon—carbon double bond that is present within PPF, which enables it to participate in the crosslinking reaction. Furthermore, DEF will not significantly alter the biomaterial properties of the purely PPF materials that have been investigated previously.

While the description below describes a preferred embodiment of the invention in which DEF is used as the fumarate precursor, other fumarate derivatives, including but not limited alkyl fumarates such as dimethyl fumarate, methyl ethyl fumarate, diisopropyl fumarate, dibutyl fumarate, are equally useful in the invention.

In order to quantify the effectiveness of the present crosslinked systems, the photocrosslinking characteristics and mechanical properties of DEF/PPF biomaterials have been characterized and determined according to their dependence on three factors: PPF molecular weight, BAPO photoinitiator content, and DEF content. In particular, the present invention relates to the effects of these factors on (1) uncured DEF/PPF solution viscosity, (2) DEF/PPF photocrosslinking reaction extent as measured by heat evolution and sol fraction, and (3) cured DEF/PPF mechanical properties. Definition of the DEF/PPF photocrosslinking characteristics and mechanical properties as described herein will make it possible to realize the potential of these novel fumarate-based biomaterials as well as describe the crosslinking of a polymer/polymer precursor system.

Experimental Design

For the purpose of determining the relative effects of several variables without requiring impractical numbers of trials, a three factor, factorial design was devised. The three factors investigated were (1) poly(propylene fumarate) number average molecular weight (PPF $M_n$), (2) bis(2,4,6 trimethylbenzoyl) phenylphosphine oxide content (mg BAPO/g (DEF+PPF)), and (3) diethyl fumarate content (g DEF/g PPF). The first two factors were each investigated at two levels (0 and 1), while the third factor, diethyl fumarate content, was investigated at four levels (0, 1, 2, and 3). For the first factor, poly(propylene fumarate) number average molecular weight (PPF $M_n$, g/mol), the low value (0) was set at 1260 g/mol and the high value (1) was set at 2260 g/mol. For the second factor, bis(2,4,6 trimethylbenzoyl) phenylphosphine oxide content, the low value (0) was selected to be 2.5 mg BAPO/g (DEF+PPF) and the high value (1) was selected to be 5.0 mg BAPO/g (DEF+PPF). For the third value, diethyl fumarate content, the four values (0, 1, 2, and 3) were set at 0.00, 0.33, 1.00 and 3.00 g DEF/g PPF, respectively. Thus a 2×2×4 design, comprised 16 formulations, was investigated; Table 1 presents the composition of all formulations.

TABLE 1

Outline of the three factor, 2 × 2 × 4 factorial design.

| Sample Number | PPF Molecular Weight (Mn, g/mol) | BAPO Initiator Content (mg BAPO/g (PPF + DEF)) | DEF Content (wt %) |
|---|---|---|---|
| 1 | L, 1260 | L, 2.5 | 0%, L |
| 2 | L, 1260 | L, 2.5 | 25%, ML |
| 3 | L, 1260 | L, 2.5 | 50%, MH |
| 4 | L, 1260 | L, 2.5 | 75%, H |
| 5 | L, 1260 | H, 5.0 | 0%, L |
| 6 | L, 1260 | H, 5.0 | 25%, ML |
| 7 | L, 1260 | H, 5.0 | 50%, MH |
| 8 | L, 1260 | H, 5.0 | 75%, H |
| 9 | H, 2260 | L, 2.5 | 0%, L |
| 10 | H, 2260 | L, 2.5 | 25%, ML |
| 11 | H, 2260 | L, 2.5 | 50%, MH |
| 12 | H, 2260 | L, 2.5 | 75%, H |
| 13 | H, 2260 | H, 5.0 | 0%, L |
| 14 | H, 2260 | H, 5.0 | 25%, ML |
| 15 | H, 2260 | H, 5.0 | 50%, MH |
| 16 | H, 2260 | H, 5.0 | 75%, H |

It should be understood that the values that were selected as the high, low, and intermediate values for each of the three factors above have no particular significance with respect to the invention and are not intended to represent upper or lower limits, or to have any significance other than their relative values and their ability to illustrate the relative effect of various parameters on the system.

Poly(Propylene Fumarate) Synthesis

Poly(propylene fumarate) was synthesized following a two step procedure [11]. First, 1 mole of diethyl fumarate (Acros Organics, Pittsburgh, Pa.) and 3 moles of 1,2 propanediol (Acros Organics) were reacted using 0.01 moles $ZnCl_2$ (Fisher Chemicals, Fair Lawn, N.J.) as a catalyst and 0.002 moles hydroquinone (Acros Organics) as a radical inhibitor. The reaction was run under a nitrogen blanket, producing bis(hydroxypropyl) fumarate as the main product and ethanol as a byproduct. Second, the bis(hydroxypropyl) fumarate was transesterified, producing poly(propylene fumarate) and 1,2 propanediol as a byproduct.

Since the number average molecular weight ($M_n$) of PPF generally increases with increasing transesterification temperature and time, the reaction was run until the product had the desired molecular weight (see above), as determined by gel permeation chromatography. The PPF product was dissolved in methylene chloride (Fisher Chemicals) for purification. PPF was first washed with acid (5 wt % HCl in $H_2O$) to remove the $ZnCl_2$ and then purified with two washes each of both pure water and brine. The organic phase was then dried with sodium sulfate. Next, the PPF was precipitated in ethyl ether twice to remove the hydroquinone. The excess ether was then decanted. The remaining solvents were finally removed from the PPF by rotary evaporation followed by vacuum drying. $M_n$ typically rises after purification as lower molecular weight chains are removed by the aqueous washes. The final product was a clear, light yellow viscous liquid. Two PPF samples were synthesized: a short chain sample ($M_n$=1260±0, P.I.=1.4±0.0, and average number of double bonds per PPF chain=7.6) and long chain sample ($M_n$=2260±0, P.I.=1.7±0.0, and average number of double bonds per PPF chain=14.0).

Gel Permeation Chromatography

The molecular weight distributions of PPF were determined by gel permeation chromatography (GPC). The GPC system included an HPLC pump (Waters, Model 510, Milford, Mass.), an autosampler (Waters, Model 717), a chromatography column (Waters, Styragel HR 4E, 7.8×300 mm column [50–100,000 Da range]), and a differential refractometer (Waters, Model 410). The solvent, degassed chloroform, was run at 1.0 ml/min for sample measurement. Polystyrene standards (500, 2630, 5970, and 18100 Da) were used to obtain a calibration curve for calculating molecular weight distributions. Each sample type was run in triplicate; the reported values ($M_n$ and P.I.) are the mean values and the associated errors are the standard deviations.

DEF/PPF Photocrosslinking

The diethyl fumarate/poly(propylene fumarate) formulations were crosslinked with ultraviolet light using the photoinitiator bis(2,4,6-trimethylbenzoyl) phenylphosphine oxide (BAPO, Ciba Specialty Chemicals, Tarrytown, N.Y.). As shown in FIG. 1, the significant reactions include the direct crosslinking between two PPF chains as well as the crosslinking of two PPF chains by polymerized DEF.

For the formulations that did not contain DEF, BAPO was first dissolved in methylene chloride (0.05 ml/g PPF). The uncrosslinked PPF solution was warmed to approximately 50° C., allowing the viscous polymer to become fluid, and then mixed with the BAPO solution to achieve the appropriate initiator content.

For the formulations that did contain DEF, the appropriate amount of BAPO initiator was first dissolved into DEF and then the corresponding amount of PPF was mixed into the DEF/BAPO solution. The final solution was poured into a cylindrical glass vial (6.5 mm×40 mm). Vials were then centrifuged (5 min at 3000 rpm) if the final solution was viscous enough to retain air bubbles. The samples were photocrosslinked using an Ultralum (Paramount, Calif.) ultraviolet light box. This UV box is outfitted with four 15W, long wavelength UV bulbs and its interior reflects UV light. The total light emission covers a range of UV wavelengths (320–405 nm), with a peak at 365 nm and an intensity of approximately 2 mW/$cm^2$ at 10 cm. The BAPO photoinitiator absorbs wavelengths below 400 nm, with a general increase in absorption as the wavelength decreases to 200 nm. All of the samples were exposed to ultraviolet light for 30 minutes at a distance of approximately 10 cm. Samples were placed on their sides in a Pyrex petri dish that was elevated from the floor of the UV box. This configuration allows the incident light to penetrate the cylindrical samples radially from all sides.

Differential Photocalorimetry

Differential photocalorimetry (DPC) was performed using a differential scanning calorimeter (Model 2920, TA Instruments, New Castle, Del.) fitted with a DPC module (Model DSC2910, TA Instruments). The UV light (200 W Hg lamp whose characteristic wavelengths include 313, 366, 405 and 435 nm) was corrected for any uneven distribution over both the sample and reference in the chamber. The reference was a cured sample of photocrosslinked DEF/PPF whose formulation was identical to the test sample. Heat flux was measured during UV exposure under isothermal conditions and after chamber equilibration at 37° C. The heat release due to UV initiated crosslinking was calculated as the area beneath the heat flux curve with a baseline drawn coincident with the plateau region between 5 and 30 min. Each sample type was run in triplicate; the reported values are the mean values and the associated errors are the standard deviations.

Photocrosslinking Reaction Temperature

The interior temperature of DEF/PPF samples during ultraviolet light exposure was measured using a wire thermocouple. Uncured samples were first prepared in 6.5 mm diameter glass vials as previously described. A 0.025 mm diameter, Teflon insulated wire thermocouple (Omega Engineering, Stamford, Conn.) was then inserted into the sample. The thermocouple tip was kept at least 10 mm from the end of the glass vial as well as away from the side of the glass cylinder, but no radial position was specified. The sample with thermocouple was then placed within the UV box. Temperature was recorded at 1 Hz for 4000 s using an InstruNet data acquisition box and software program (Nordisk Transducer Teknik, Hadsund, Denmark). Ultraviolet light exposure lasted from t=100 to 1900 s only, with the remainder of the experiment occurring in the dark. The maximum reaction temperature was defined as the local maximum temperature between approximately t=200 and 800 s. The time to maximum reaction temperature was defined as the time from the ignition of the UV light (t=100 s) to the time at which the maximum reaction temperature was recorded. Each sample type was run in triplicate; the reported values are the mean values and the associated errors are the standard deviations.

Rheometry

The solution viscosity was determined using a rheometer (Model AR1000, TA Instruments). Due to the wide range of viscosities that were to be tested, a modified parallel plate system was utilized so that all sample types could be tested in the same manner. The sample solution was placed into a Teflon mold (10 mm diameter and 15 mm depth) positioned on the temperature controlled plate of the rheometer. The temperature was set at 37° C. An 8 mm diameter, cylindrical parallel plate geometry was lowered into approximately 0.5 ml of the sample contained within the mold. A continuous flow program, with shear strain held at 10 Pa, was run for 300 s and viscosity was monitored throughout the experiment. The value recorded for a single run was the average value over the final 200 s of the experiment. Each sample type was run in triplicate; the reported values are the mean values and the associated errors are the standard deviations.

Sol Fraction

A study of the DEF/PPF construct sol fraction was performed using photocrosslinked cylinders, approximately 0.5 g in weight, whose fabrication was described previously. A photocrosslinked sample was weighed ($W_i$) and placed into 20 ml of methylene chloride, as both PPF and DEF are soluble in this organic solvent but crosslinked DEF/PPF networks are not. Vials containing the samples in methylene chloride were capped and then stirred at 75 rpm for approximately 160 hrs. Samples, most of which had crumbled, were then removed from the solvent by pouring the mixture through a weighed filter paper ($W_p$). The filter paper containing the sample was dried for 1 hr at 60° C. and then weighed again ($W_{p+s}$). The sol fraction of the sample was then calculated using the formula:

$$\text{Sol Fraction} = \frac{W_i - (W_{p+s} - W_p)}{W_i} \times 100\%. \quad (1)$$

Each sample type was run five times; the reported values are the mean values and the associated errors are the standard deviations.

Compressive Mechanical Testing

Compressive testing of DEF/PPF constructs were conducted using a mechanical testing system (Model 858, MTS System Corporation, Eden Prairie, Minn.). Cylindrical samples were synthesized as described previously and then cut to proper length; typical sample sizes were 6.5 mm in diameter and 13.0 mm in length. Force and displacement were zeroed prior to compression, with the top plate slightly above the surface of the sample. Samples were compressed at a crosshead speed of 1 mm/min while stress and strain were monitored throughout the experiment. The experiment was halted after sample fracture. The initial slope of the stress-strain curve determined the elastic modulus of the sample. Compressive strength at fracture was defined as the stress required to fracture the material. Each sample type was run five times; the reported values are the mean values and the associated errors are the standard deviations.

Statistics

The results of the 2×2×4 factorial design were inspected by an analysis of variance (ANOVA) [12]. As three factors were investigated, a total of seven treatments were possible: 3 main factor effects, 3 two factor interaction effects, and 1 three factor interaction effect. (For example, in a study of factors A, B, and C, the main effects are A, B, and C, the two factor interaction effects are AB, AC, and BC, and the three factor interaction is ABC.) An F value, F critical value, and p value were then calculated for each of the seven treatments; p values are indicated. A significance level of 95% ($\alpha=0.05$) was chosen, thus a treatment with a p value less than 0.05 is considered to be significant determinant of the response. While all treatments were investigated in this manner, only the main effects are discussed below.

Results

Solution Viscosity

Figure 2:
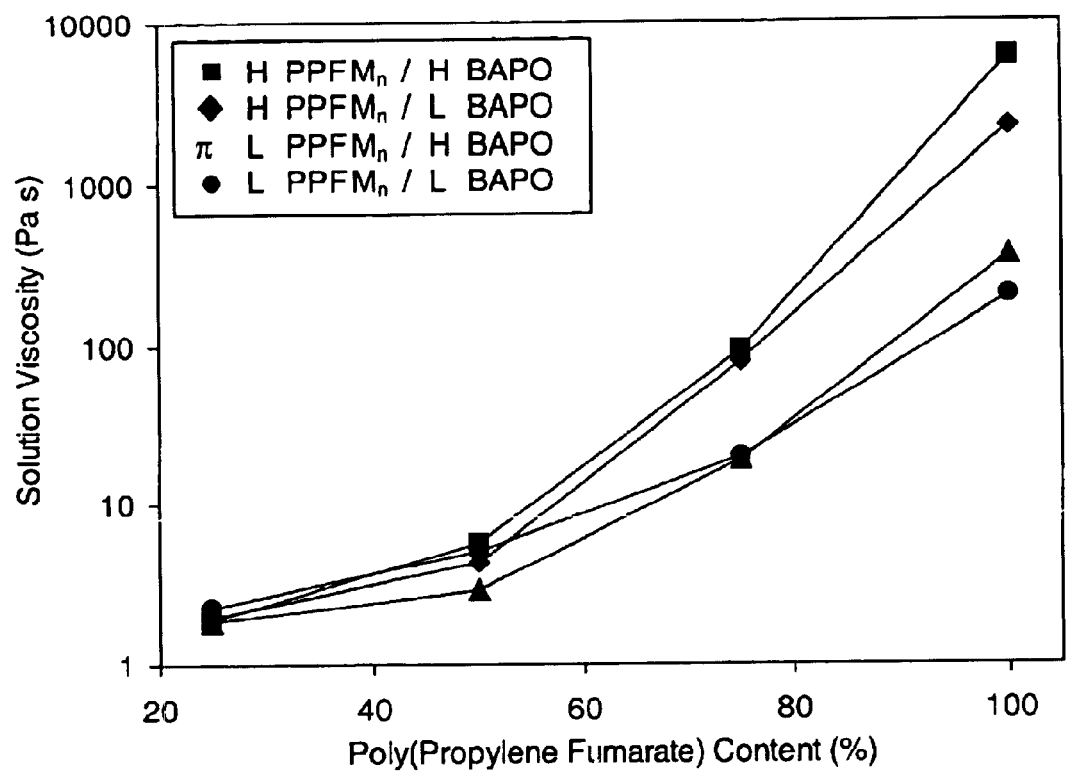
FIG. 2 is a plot showing the effect of PPF molecular weight, BAPO content, and DEF content on the uncured solution viscosity.

The viscosities of the uncured DEF/PPF solutions were found to fall over three orders of magnitude, from 5940 to 2 Pa s, as DEF content is increased from 0 to 75%, as shown in FIG. 2. FIG. 2 plots the effect of PPF molecular weight, BAPO content, and DEF content on the uncured solution viscosity. Note that error bars are too small to appear. All factors, PPF molecular weight ($p=1.3\times10^{-8}$), BAPO content ($p=7.2\times10^{-4}$), and DEF content ($p=2.9\times10^{-14}$) were found to be significant in determining uncured solution viscosity. Analysis of the results from the factorial design study showed that PPF molecular weight, BAPO content, and DEF content to be statistically significant factors determining viscosity, though BAPO content was found to be a weak factor. Increases in PPF molecular weight and decreases in DEF content act to increase uncured DEF/PPF solution viscosity.

Heat Release During Photocrosslinking

Figure 3:
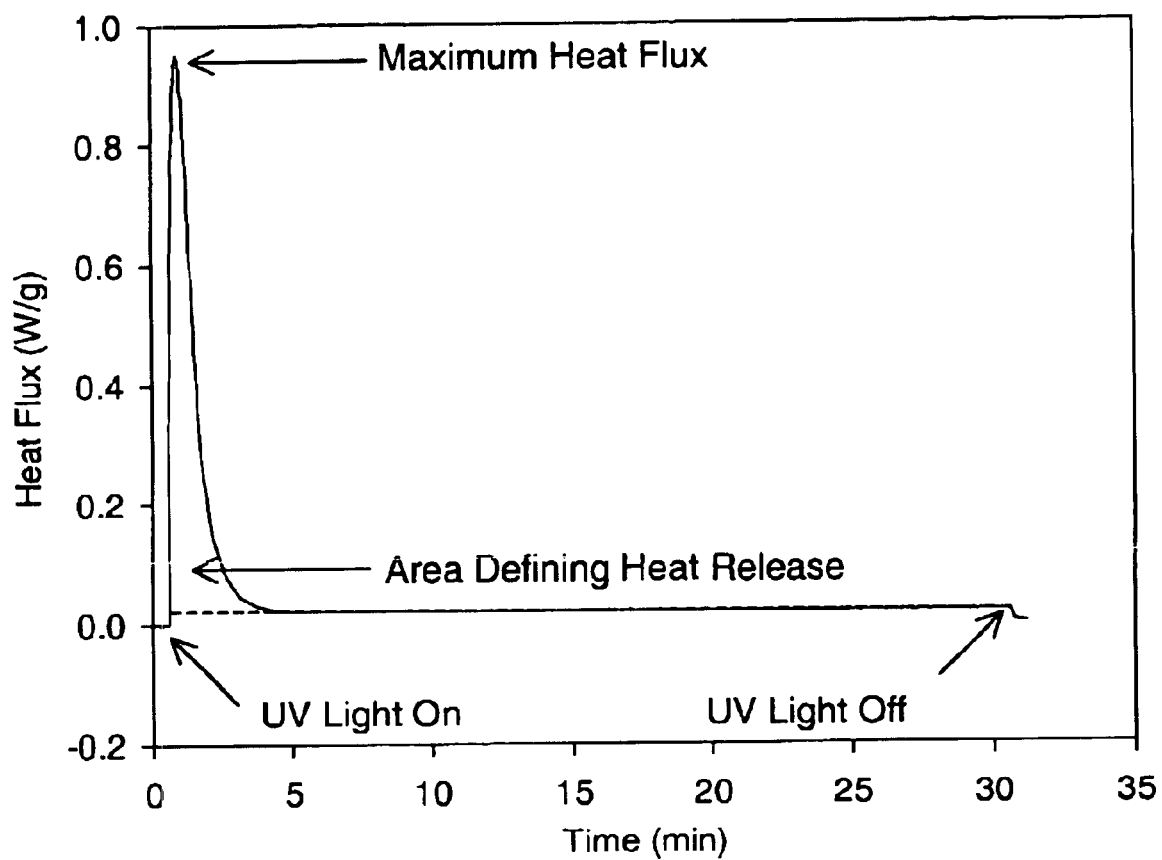
FIG. 3 is a plot of heat flux from the photocrosslinking reaction of DEF/PPF, using a formulation comprising 1260 g/mol $M_n$ PPF, 2.5 mg BAPO/g (PPF+DEF), and 75% DEF.

The heat flux produced from the photocrosslinking reaction during 30 min of ultraviolet light exposure was measured using a differential photocalorimeter. A heat flux curve for Sample # 3 is shown in FIG. 3 and is generally representative of nature of the heat flux curves for other samples. Ultraviolet light exposure occurred between t=0.5 and 30.5 min, lasting for a total of 30 min. The cumulative heat release was calculated as the area beneath the heat flux curve, with a baseline drawn coincident with the plateau region between 5 and 30 min.

Figure 4A:
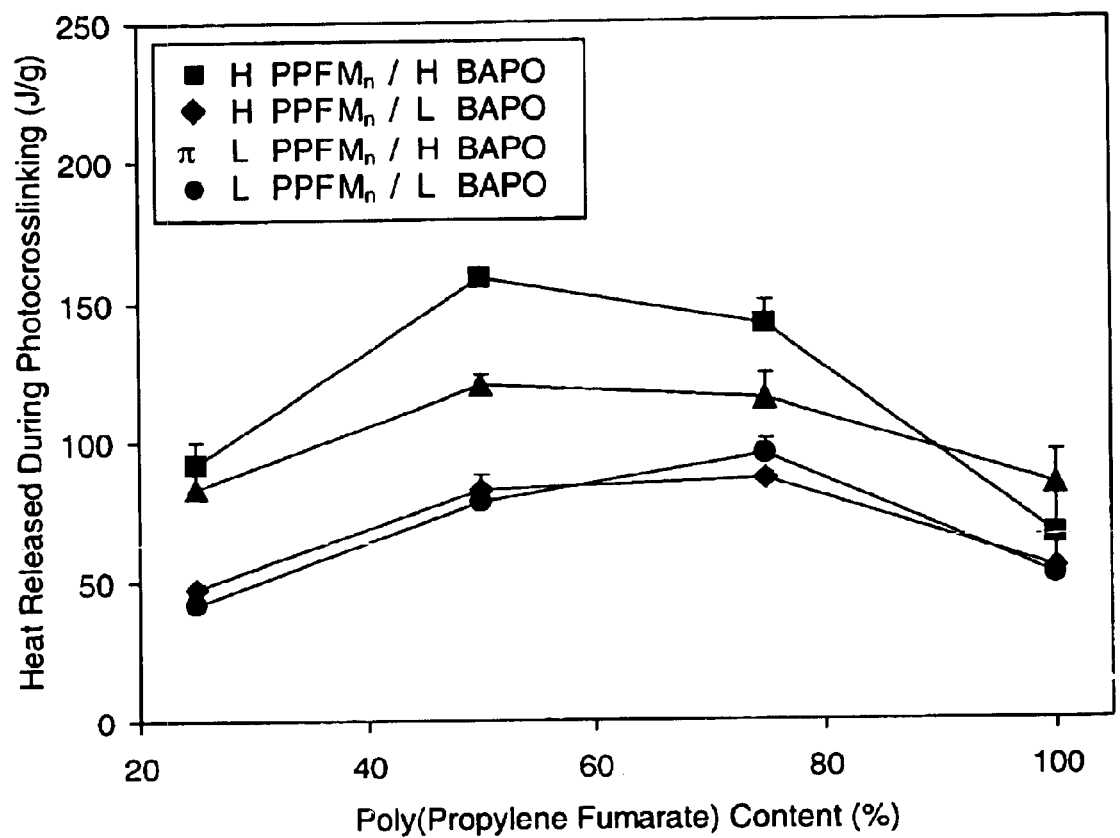
FIGS. 4A–B are plots showing the effect of PPF molecular weight, BAPO content, and DEF content upon the photocrosslinking reaction heat release and the time to maximum heat release, respectively.
Figure 4B:
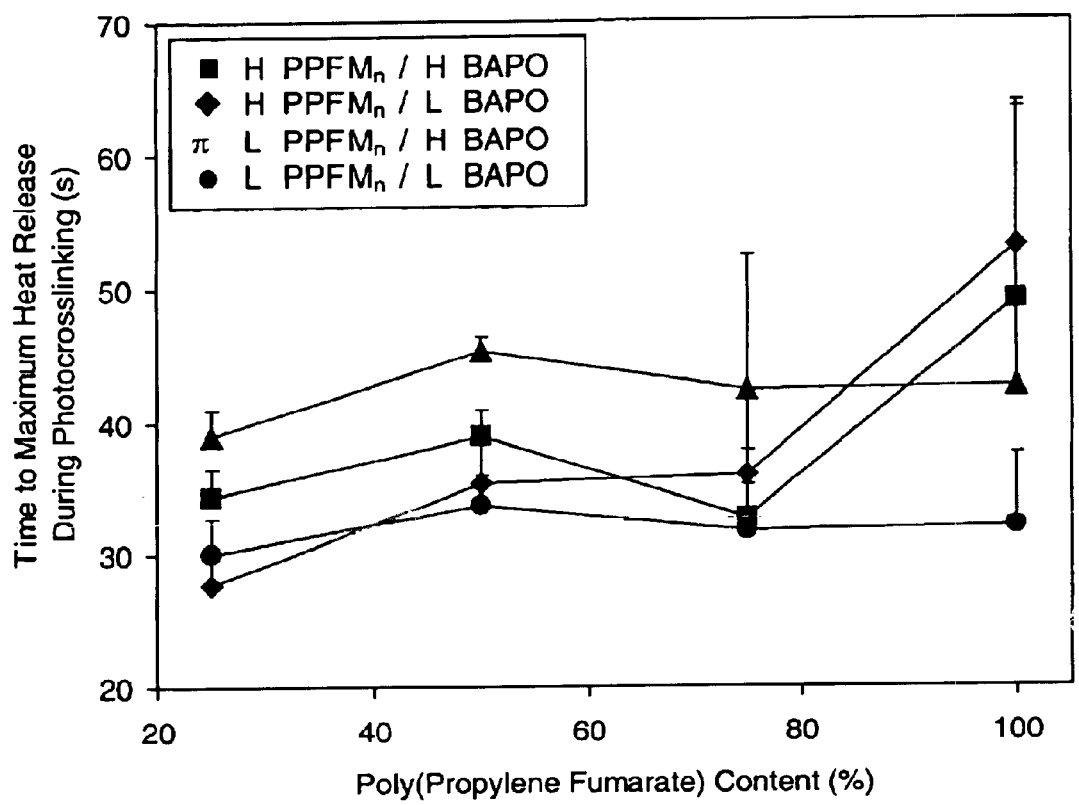

Heat release varied between 41.9 and 158.4 J/g, with the greatest values found in those formulations containing 25–50% DEF content. FIGS. 4A–B shows the effect of PPF molecular weight, BAPO content, and DEF content on the photocrosslinking reaction heat release (A) and the time to maximum heat release (B). (See Table 1 above for a description of the sample formulations.) The heat release results (A) are compared to the theoretical heat evolution that would occur if all of the DEF and varying numbers of fumarate bonds within the PPF polymer (n=1 to 14, where 14 is the theoretical number based upon a PPF $M_n$ of 2260 g/mol) were to have reacted.

All factors, PPF molecular weight ($p=4.4\times10^{-3}$), BAPO content ($p=1.9\times10^{-17}$), and DEF content ($p=3.1\times10^{-17}$), were found to be significant in determining heat release. BAPO content ($p=6.2\times10^{-3}$) and DEF content ($p=1.6\times10^{-3}$) were found to be significant in determining the time to maximum heat release; PPF molecular weight ($p=5.1\times10^{-1}$) was found to be an insignificant factor. Results of the factorial design indicated that PPF molecular weight, BAPO content, and DEF content all have statistically significant effects upon heat release during the photocrosslinking reaction. Maximum heat release occurs between 28 and 53 s after initiation of ultraviolet light exposure (FIG. 4B). Statistical analysis of the results show that BAPO content and DEF content had a statistically significant effect upon the time to maximum heat release.

Photocrosslinking Reaction Temperature

Figure 5:
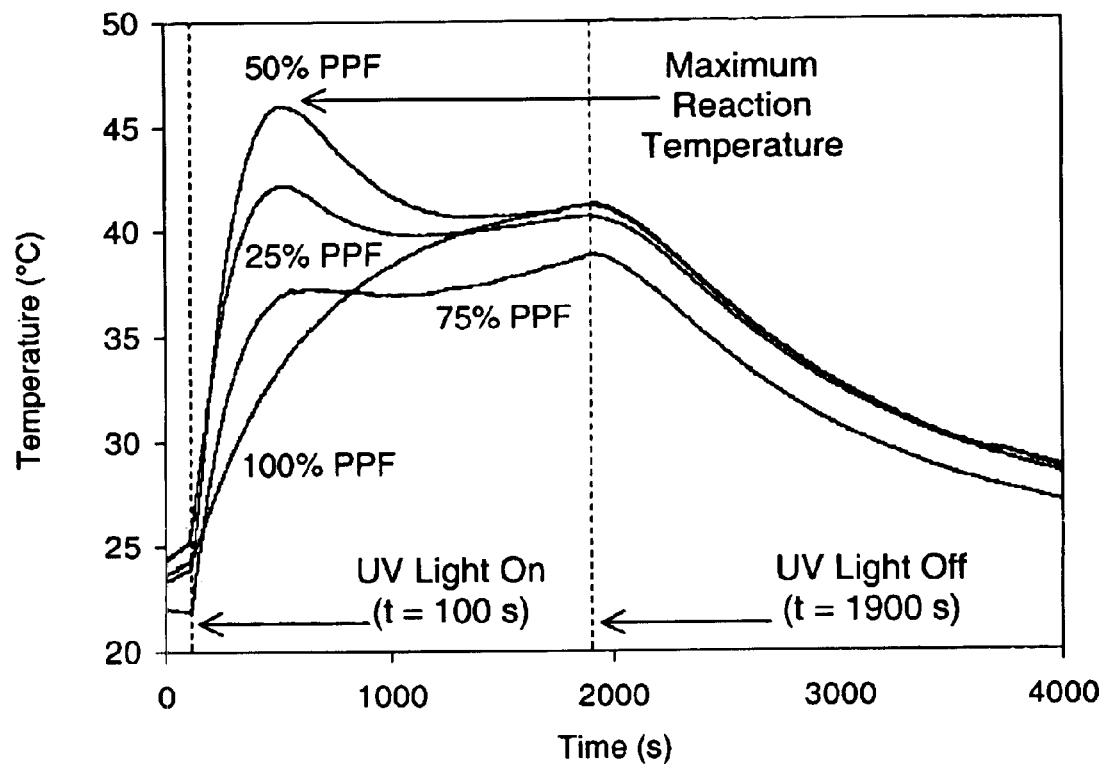
FIG. 5 is a plot of temperature profiles for four DEF/PPF formulations with varying DEF content (all contain 2260 g/mol $M_n$ PPF and 2.5 mg BAPO/g (PPF+DEF))

Interior temperatures of DEF/PPF samples during and after the photocrosslinking reaction were monitored using a wire thermocouple. The results (FIG. 5) show that a local maximum temperature occurs in early experimental times for formulations containing DEF, but not in formulations containing only PPF. FIG. 5 is a plot of temperature profiles for Samples # 9, 10, 11, and 12 (all contain 2260 g/mol $M_n$ PPF and 2.5 mg BAPO/g (PPF+DEF)). All formulations that contain DEF were found to exhibit a local maximum temperature at approximately 500 s. This temperature was identified as the maximum reaction temperature. The time to maximum reaction temperature was defined as the time from the ignition of the UV light (t=100 s) to the time at which the maximum reaction temperature was recorded. This first local peak likely reflects the exothermic photocrosslinking reaction. The second local peak at 1900 s, found in all samples, is due to the warming effects of the ultraviolet light, as the fall in sample temperature occurs immediately following the cessation of UV light exposure at 1900 s (FIG. 5). Since the interest of this work lies in the photocrosslinking reaction, and not the heating effects of UV light, the samples containing only PPF were not considered in the further analyses.

Figure 6A:
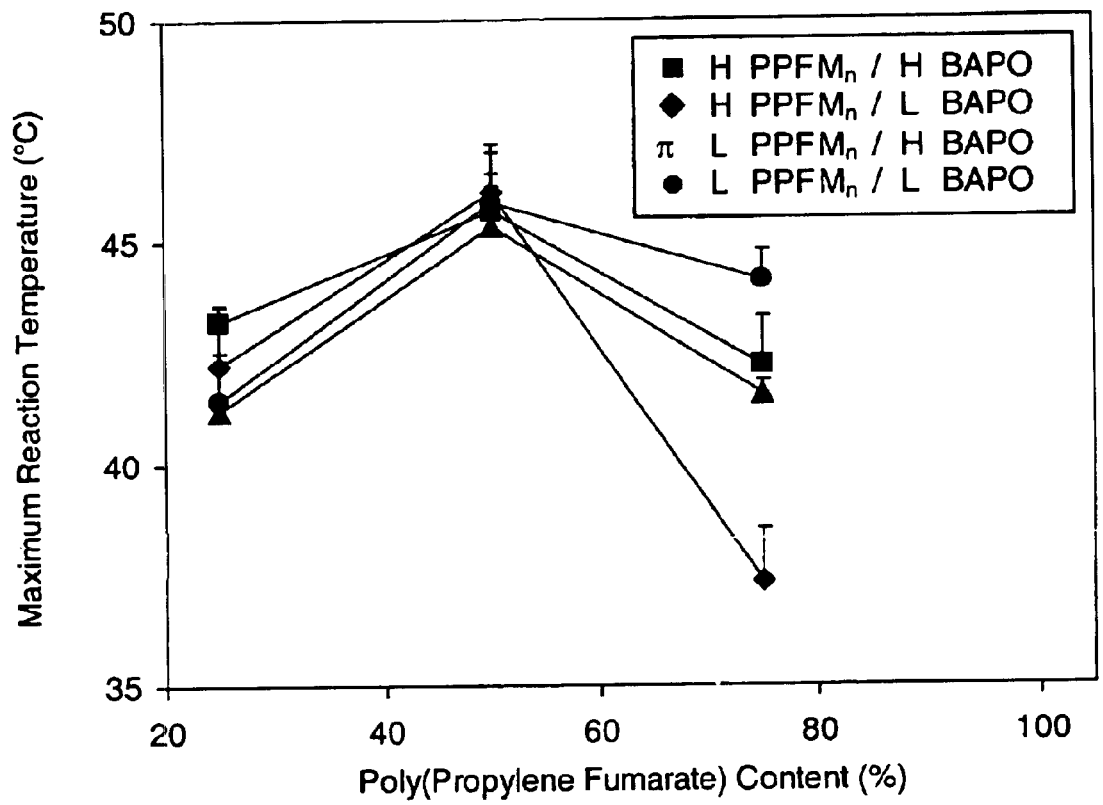
FIGS. 6A–B are plots of the effect of PPF molecular weight, BAPO content, and DEF content on the maximum reaction temperature and the time to maximum reaction temperature, respectively.
Figure 6B:
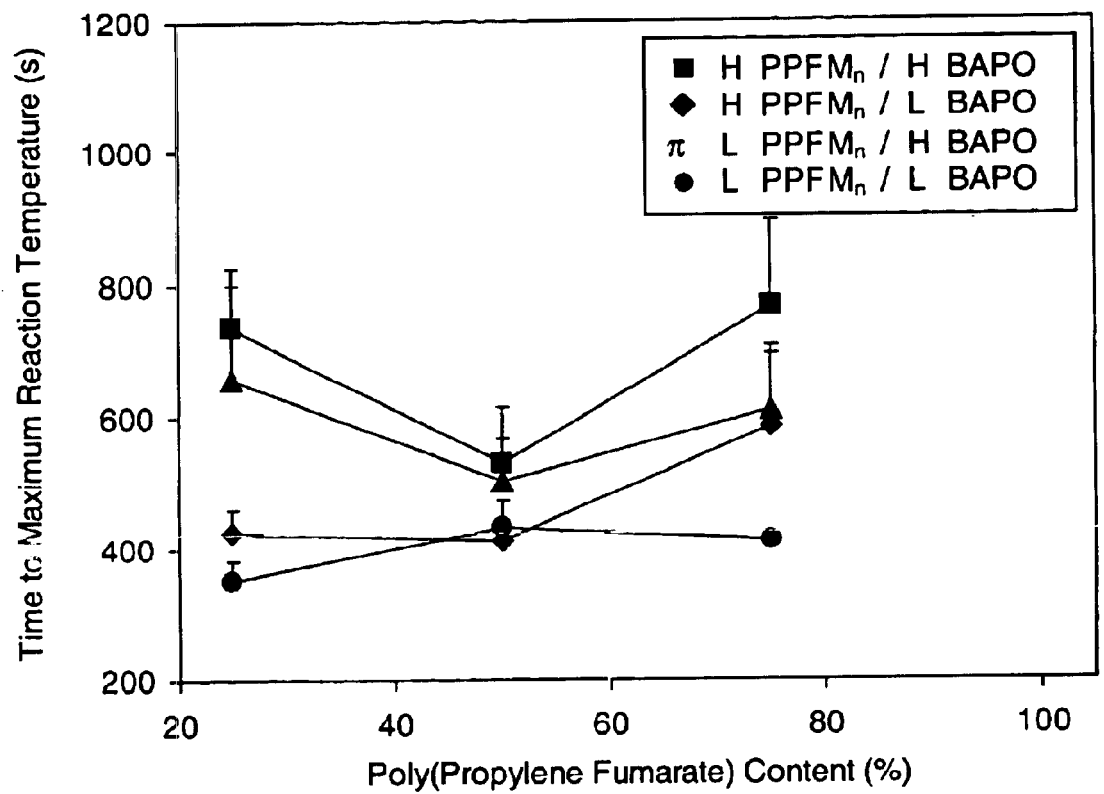

The results show that formulations containing 50% DEF generally present the highest maximum reaction temperatures. FIGS. 6A–B plot the effects of PPF molecular weight, BAPO content, and DEF content on the maximum reaction temperature and the time to maximum reaction temperature, respectively. (Again, refer to Table 1 above for a description of sample formulations.)

DEF content ($p=7.7 \times 10^{-10}$) was found to be the significant factor determining maximum reaction temperature; PPF molecular weight ($p=2.2 \times 10^{-1}$) and BAPO content ($p=3.4 \times 10^{-1}$) were found to be insignificant factors. All factors, PPF molecular weight ($p=6.6 \times 10^{-3}$), BAPO content ($p=1.9 \times 10^{-7}$), and DEF content ($p=4.1 \times 10^{-3}$), were found to be significant in determining the time to maximum reaction temperature. Analysis of the factorial design further indicates that DEF content is the significant factor determining the maximum reaction temperature. The amount of time required to achieve maximum reaction temperature was also noted in these experiments (FIG. 6B). The time to maximum reaction temperature varied from 352 to 768 s and found to be determined by PPF molecular weight, BAPO initiator content, and DEF content.

Sol Fraction

Figure 7:
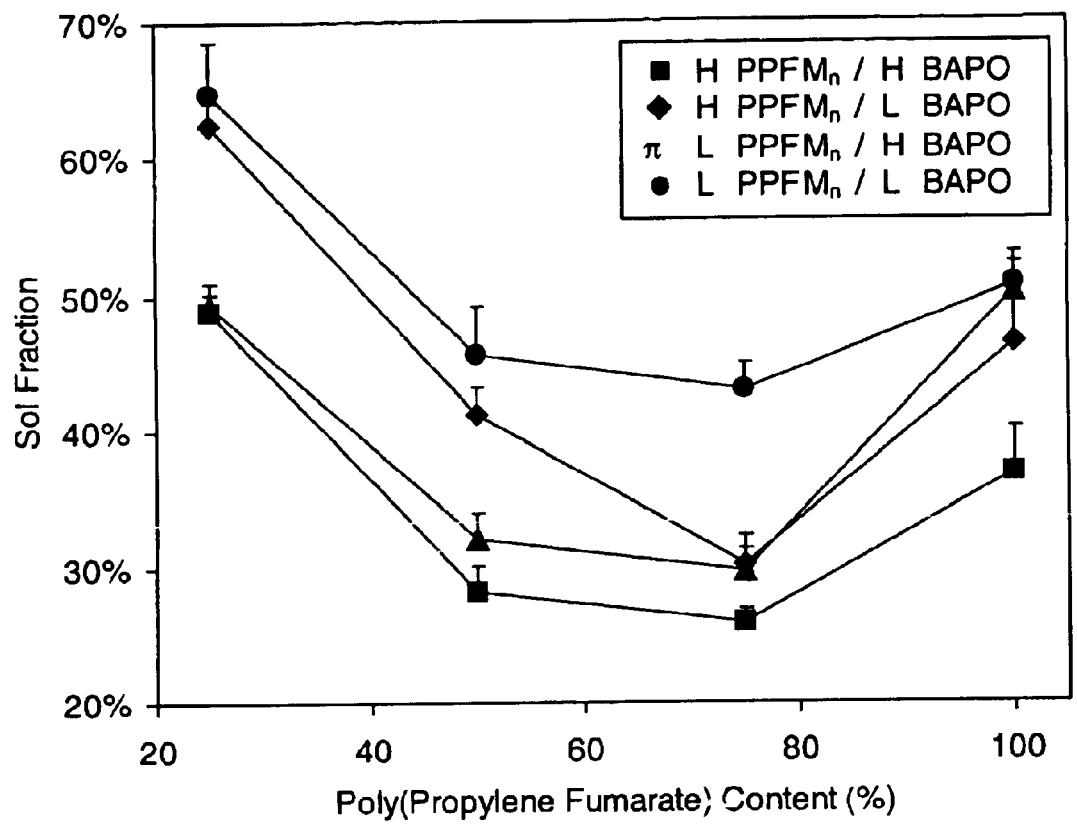
FIG. 7 is a plot of the effect of PPF molecular weight, BAPO content, and DEF content upon the sol fraction of photocrosslinked samples.

The results show that a significant fraction of all photocrosslinked DEF/PPF formulations are soluble in the methylene chloride organic solvent, implying that these fractions are not contributing to the bulk, crosslinked polymer network. FIG. 7 is a plot of the effect of PPF molecular weight, BAPO content, and DEF content upon the sol fraction of photocrosslinked samples and shows that the sol fraction for all formulations initially decreases with DEF addition, but subsequently increases when DEF content is above 25%.

All factors, PPF molecular weight ($p=1.8 \times 10^{-15}$), BAPO content ($p=2.6 \times 10^{-28}$), and DEF content ($p=6.2 \times 10^{-41}$), were found to be significant in determining the sample sol fraction. The smallest sol fractions, less than 30%, were found in those formulations containing high initiator content, high PPF molecular weight, and moderate (25–50%) DEF content. All three experimental factors, PPF molecular weight, BAPO content, and DEF content, were found to be significant in determining sol fraction.

Compressive Mechanical Properties

Figure 8A:
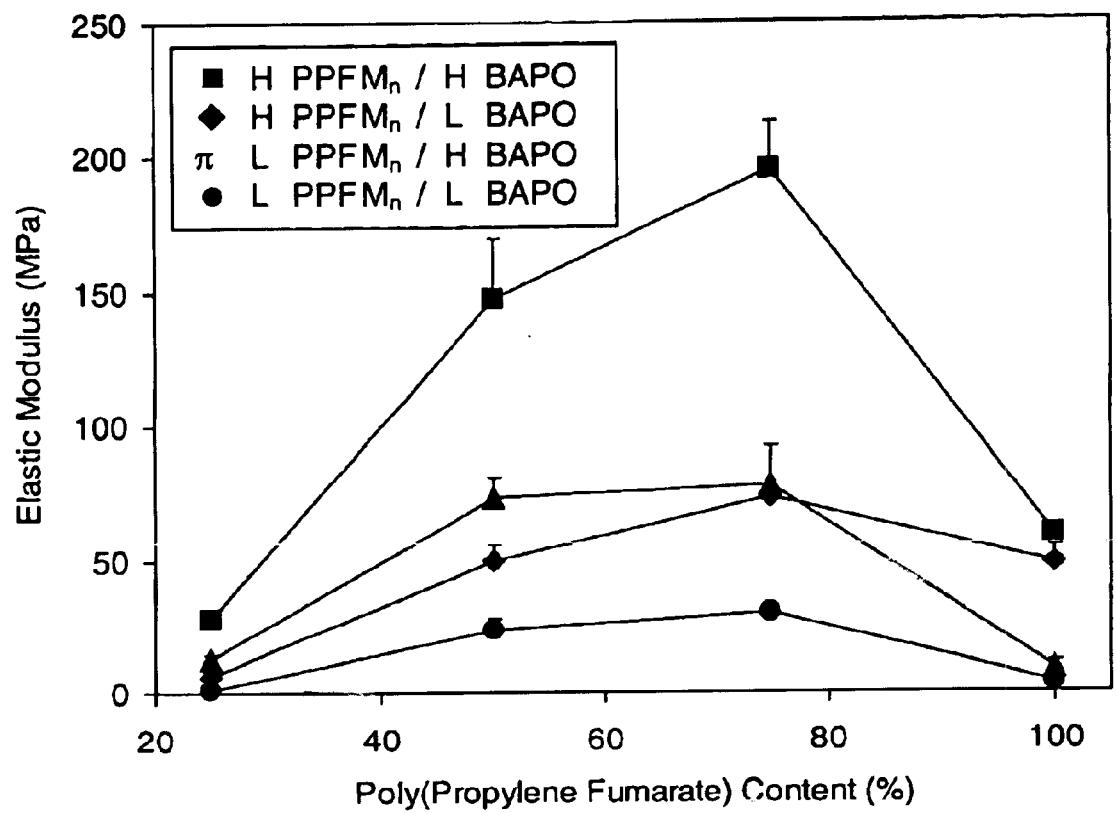
FIGS. 8A–B are plots of the effect of PPF molecular weight, BAPO content, and DEF content on photocrosslinked samples' elastic modulus and strength at fracture, respectively.
Figure 8B:
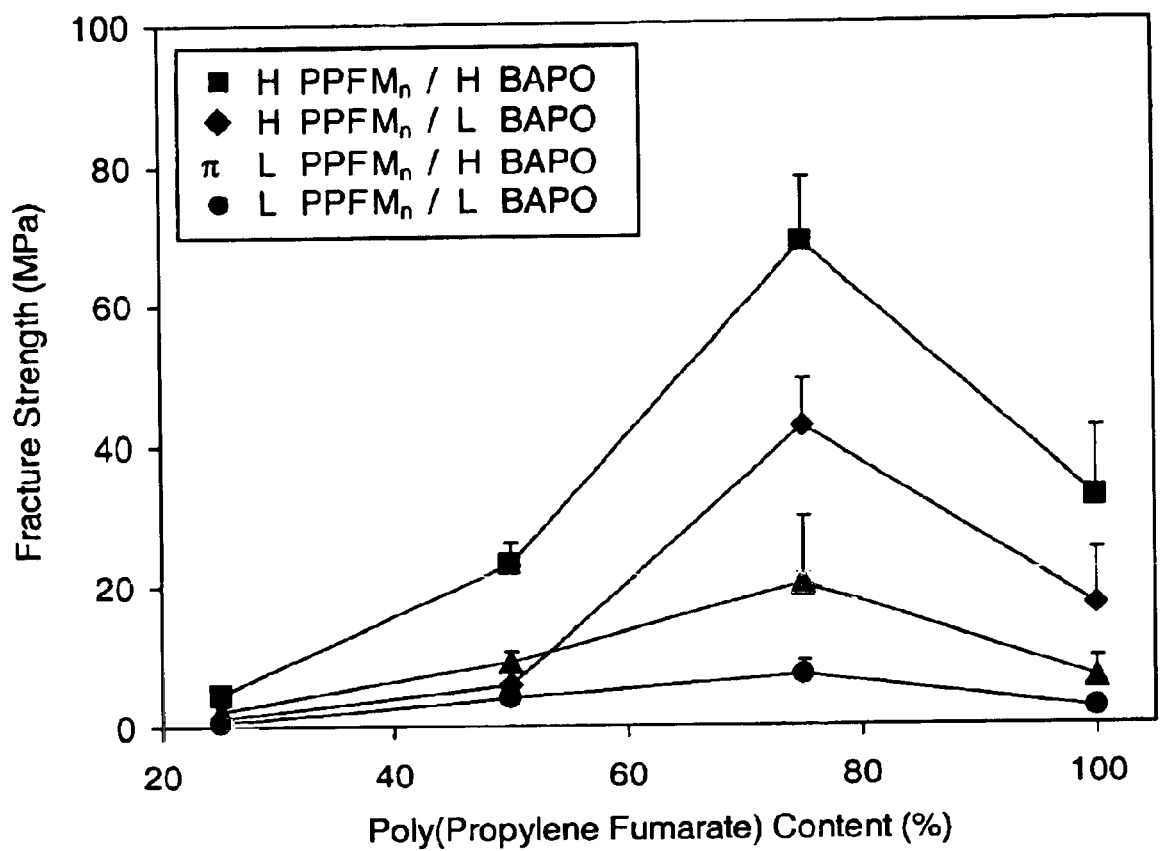

The mechanical properties of the various DEF/PPF samples were assessed by compressive mechanical testing. FIGS. 8A–B are plots of the effect of PPF molecular weight, BAPO content, and DEF content on photocrosslinked samples' elastic modulus and strength at fracture, respectively, according to the formulations set out in Table 1. All factors, PPF molecular weight ($p=1.8 \times 10^{-30}$), BAPO content ($p=1.0 \times 10^{-29}$), and DEF content ($p=2.4 \times 10^{-42}$), were found to be significant in determining elastic modulus. Similarly, PPF molecular weight ($p=1.3 \times 10^{-23}$), BAPO content ($p=7.9 \times 10^{-14}$), and DEF content ($p=1.4 \times 10^{-28}$), were found to be significant in determining fracture strength. Both elastic modulus and fracture strength were generally found to be the greatest in the formulations containing 25% DEF.

Discussion

The development of a synthetic, degradable biomaterial for tissue engineering applications is highly desirable. Photocrosslinked PPF is of interest because it may allow for the prefabrication of tissue engineering scaffolds with precisely defined external dimensions as well as interior porous structure by using techniques such as stereolithography. Alternatively, photocrosslinked PPF may be suitable for injectable applications in which it is cured either during or after its injection. In order to fully explore these options, a low viscosity form of photocrosslinkable PPF was desired, leading to the development of DEF/PPF and related biomaterials. The present work has characterized the crosslinking and mechanical properties of these novel DEF/PPF biomaterials.

The addition of DEF to PPF resulted in a reduction in viscosity, with increasing amounts of DEF lowering viscosity by over three orders of magnitude. Solution viscosity has been explored in other injectable materials proposed as bone substitutes or bone tissue engineering constructs, with viscosity controlled by the addition of calcium phosphate fillers, for example [13]. It is also interesting to note that, similar to the system described here, clinically used bone cements of polymethylmethacrylate utilize a polymer/monomer crosslinking system that allows for injectability [14]. The advantageous feature of the PPF/DEF material is that while viscosity may be lowered with DEF addition (FIG. 2), the mechanical strength of the crosslinked material is increased, so long as DEF content remains below 25–50% (FIGS. 8A and 8B). Thus, the addition of small amounts of DEF to PPF allows for a material with both improved handling characteristics and increased mechanical strength.

The second goal of this work was to characterize the extent of the DEF/PPF photocrosslinking reaction by investigating the heat evolution during the reaction and the sol fraction of the crosslinked samples. The results (FIG. 4A) indicate that the total heat evolved during the photocrosslinking reaction is low, below 160 J/g, regardless of formulation. FIG. 4A compares these results to the known heat of polymerization of diethyl fumarate (65 kJ/g) [19]. The results indicate that at low DEF content/high PPF content most of the DEF is involved in the photocrosslinking reaction, if it is assumed that the number of fumarate units within PPF reacted is low (<5 fumarate units). This seems a reasonable assumption considering the diffusional limitations restricting the PPF polymer movement as well as steric hindrances inhibiting addition to the polymer. However, at increasingly higher DEF content, FIG. 4A suggests that significant portions of both the PPF and DEF are not involved in the photocrosslinking reaction. This is supported by the results of the sol fraction study which show increasing sol fraction as DEF content is increased beyond 25% (FIG. 7).

The low heat evolution is realized in the low temperatures during and after the photocrosslinking. Specifically, the results indicate that no DEF/PPF formulation reaches temperatures above 47° C. throughout photocrosslinking. These results are encouraging for in situ curing applications where low temperatures are required so as to minimize adverse bone tissue responses that are thought to occur at temperatures as low as 53° C. [15,16]. The short times at which the maximum heat release and maximum temperatures were obtained also imply that the material cures at a clinically feasible rate, similar to polymethylmethacrylate bone cements, which cure in approximately 5–10 min [14]. Many processes for prefabricating implantable devices, such as stereolithography, would also benefit from a system which crosslinks quickly and with low heat evolution [17]. Finally, since this system is photoinitiated, even quicker curing rates may be obtained by using a more intense light source, as the light source used in this work was of quite low intensity (2 mW/cm$^2$), though quicker rates may be associated with higher levels of heat evolution.

The mechanical properties of the crosslinked DEF/PPF biomaterials were also studied. The results indicate that an optimal DEF content at approximately 25% is preferred, in order to produce the highest elastic modulus and fracture strength. In addition to the effect of DEF content, both PPF molecular weight and BAPO content affect the final mechanical properties, with increases in either producing a stronger material. The properties of photocrosslinked DEF/PPF materials are well suited for use in a bone defect, as trabecular bone has been reported to possess a compressive fracture strength of approximately 5 MPa and a compressive elastic modulus of 50–100 MPa [18], though it should be noted that when materials are formed into the porous scaffolds necessary for tissue growth their mechanical strength will decrease [7].

Figure 9:
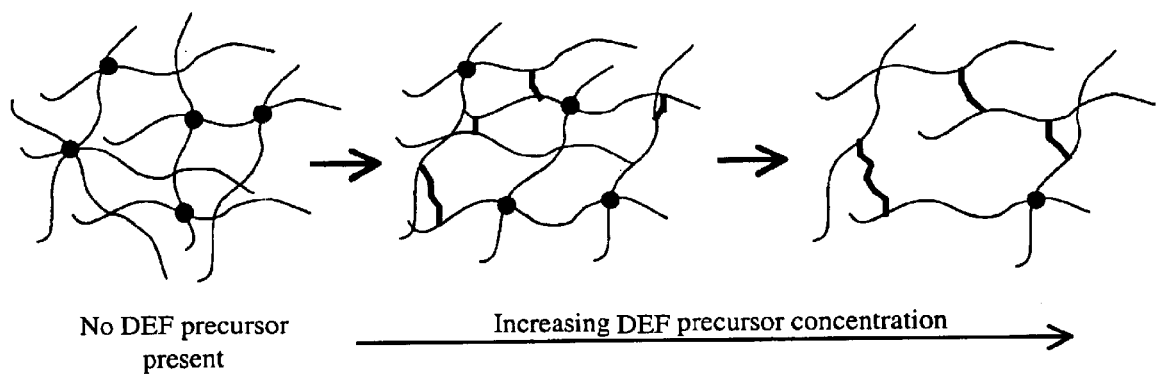
FIG. 9 is a schematic illustration of the addition of a DEF precursor to a PPF polymer.

The DEF/PPF photocrosslinking characterization also relates to how the crosslinking of a polymer is affected by the addition of the polymer's crosslinkable precursor. The concept that has been formed is that two regimes, based upon precursor content, exist: a regime of low precursor content where polymer crosslinking is facilitated and a regime of higher precursor content where polymer crosslinking is hindered. Without wishing to be bound by theory, the inventors postulate that the diagram of FIG. 9 is a schematic illustration of how the addition of a DEF precursor to a PPF polymer. may effect the structure of the formed crosslinked polymer network. On the left, adjacent PPF polymer chains, depicted as lines, are crosslinked by covalent bonds, depicted as circles, between PPF fumarate units. In the middle, PPF polymer chains are crosslinked both by covalent bonds between their fumarate units and by bridges formed by DEF precursor, depicted as linked bold line segments. On the right, PPF polymer chains are loosely linked both by covalent bonds between their fumarate units and DEF precursor bridges. The DEF precursor enhances crosslinking between PPF chains at low DEF concentrations, but hinders the crosslinking reaction at high DEF concentrations.

PPF is photocrosslinkable without the presence of a functional crosslinking monomer, such as DEF precursor, by forming covalent bonds between opened carbon—carbon double bonds on adjacent PPF chains. As DEF is added to PPF, crosslinking may be facilitated as polymerized DEF units bridge adjacent PPF chains, including those PPF chains which may have not reacted without the presence of the DEF precursor. Thus, the photocrosslinking of those formulations containing a small amount of the DEF precursor should involve the reaction of more fumarate carbon—carbon double bonds. The results presented above substantiate this concept. Solutions with 25% DEF content all release greater amounts of heat than those without DEF, implying greater numbers of carbon—carbon double bonds involved in the photocross-linking reaction. This is realized in the reduced sol fraction (FIG. 7), increased elastic modulus (FIG. 8A), and increased fracture strength (FIG. 8B) of these formulations.

However, as increasing amounts of the DEF precursor are added to the DEF/PPF solution, an opposing force of dissolution begins to dominate the system. Here the PPF polymer chains dissolved within the DEF precursor are separated by ever greater distances. While polymerized DEF units at lower DEF concentrations could bridge these gaps between PPF chains, at higher concentrations this becomes increasingly difficult. Thus, fewer fumarate units are involved in the photocrosslinking reaction. Again, the results described earlier support the concept; at DEF concentrations of 50–75% heat release upon photocrosslinking decreases (FIG. 4A), the sol fraction of the crosslinked samples increases dramatically (FIG. 7), and the mechanical properties of the cured samples falls (FIGS. 8A and 8B). Finally, this concept is substantiated by the fact that without the PPF polymer, DEF alone is not photocrosslinkable into a solid under the conditions described in this work.

Porous Scaffolds

The novel biomaterials disclosed herein can be used in any application in which an implantable device is required. One such application is the use of bone scaffolds. In particular, porous scaffolds can be formed, by polymerizing the compositions disclosed herein in the presence of a porogen, such as are known in the art. Once the network is formed, the porogen can be removed, such as by leaching, leaving the desired pores.

Conclusions

The novel biomaterials disclosed herein are based on the polymer poly(propylene fumarate) and its fumarate precursors. One preferred embodiment is diethyl fumarate, the crosslinkable unit contained within the repeating unit of PPF. PPF is soluble in other fumarate derivatives, including alkyl fumarates. It is contemplated that the principles disclosed in can be applied to any combination of PPF with a fumarate derivative in which the PPF is soluble.

The inventors have investigated the photocrosslinking characteristics and material properties of these materials, particularly for use as an engineered bone graft, and have shown that these new materials have low viscosities, crosslink with low levels of heat release, and possess mechanical properties similar to human trabecular bone. The results also indicate that in this polymer/polymer precursor system, crosslinking is facilitated at low precursor concentrations but hindered at higher precursor concentrations. Thus, the novel PPF materials disclosed herein are an attractive option for bone tissue engineering applications.

REFERENCES

1. Temenoff J S, Mikos A G. Injectable biodegradable materials for orthopedic tissue engineering. Biomaterials 2000;21:2405–2412.
2. Lee K Y, Alsberg E, Mooney D J. Degradable and injectable poly(aldehyde guluronate) hydrogels for bone tissue engineering. J Biomed Mater Res 2001;56:228–233.
3. Gauthier O, Bouler J M, Weiss P, Bosco J, Daculsi G, Aguado E. Kinetic study of bone ingrowth and ceramic resorption associated with the implantation of different injectable calcium-phosphate bone substitutes. J Biomed Mater Res 1999;47:28–35.
4. Frankenburg E P, Goldstein S A, Bauer T W, Harris S A, Poser R D. Biomechanical and histological evaluation of a calcium phosphate cement. J Bone and Joint Surg 1998;80A:1112–1124.
5. Iooss P, Le Ray A M, Grimandi G, Daculsi G, Merle C. A new injectable bone substitute combining poly($\square$-caprolactone) microparticles with biphasic calcium phosphate granules. Biomaterials 2001;22:2785–2794.

6. He S, Timmer M, Yaszemski M J, Yasko A W, Engel P S, Mikos A G. Synthesis of biodegradable poly(propylene fumarate) networks with poly(propylene fumarate)-diacrylate macromers as crosslinking agents and characterization of their degradation products. Polymer 2000;42:1251–1260.
7. Fisher J P, Holland T A, Dean D, Engel P S, Mikos A G. Synthesis and properties of photocrosslinked poly (propylene fumarate) scaffolds. J Biomater Sci Polym Ed 2001;12:673–687.
8. Fisher J P, Vehof J W M, Dean D, van der Waerden J P C M, Holland T A, Mikos A G, Jansen J A. Soft and hard tissue response to photocrosslinked poly(propylene fumarate) scaffolds. J Biomed Mater Res In press.
9. Vehof J W M, Fisher J P, Dean D, van der Waerden J P C M, Spauwen P H M, Mikos A G, Jansen J A. Bone formation in transforming growth factor beta-1 coated porous poly(propylene fumarate) scaffolds. J Biomed Mater Res In press.
10. Fisher J P, Dean D, Engel P S, Mikos A G. Photoinitiated polymerization of biomaterials. Ann Rev Mat Res 2001;31:171–181.
11. Shung A K, Timmer M D, Jo S, Engel P S, Mikos A G. Kinetics of poly(propylene fumarate) synthesis by step polymerization of diethyl fumarate and propylene glycol using zinc chloride as a catalyst. J Biomater Sci Polym Ed In press.
12. Neter J, Wasserman W, Kutner M H. Applied linear statistical models. Homewood, Ill.: Richard D. Irwin, Inc, 1985. p.798–843.
13. Grimandi G, Weiss P, Millot F, Daculsi G. In vitro evaluation of a new injectable calcium phosphate material. J Biomed Mat Res 1998;39:660–666.
14. Kuhn K D. Bone cements. Berlin, Germany: Springer-Verlag, 2000. p.21–26.
15. Wilcox C W, Wilwerding T M, Watson P, Morris J T. Use of electrosurgery and lasers in the presence of dental implants. Int J Oral Maxillofac Implants 2001;16:578–582.
16. Eriksson A, Albrektsson T, Grane B, McQueen D. Thermal injury to bone. A vital-microscopic description of heat effects. Int J Oral Surg 1982;11:115–121.
17. Jacobs P F. Stereolithography and other RP&M technologies. New York, N.Y.: American Society of Mechanical Engineers Press, 1996. p.27–80.
18. Athanasiou K A, Zhu C F, Lanctot D R, Agrawal C M, Wang X. Fundamentals of biomechanics in tissue engineering of bone. Tissue Eng, 2000;6:361–381.
19. Brandrup J, Immergut E H, Editors. Polymer Handbook. New York, N.Y.: Wiley Interscience, 1989. p.II.300.

We claim:

1. An injectable, in situ photo-crosslinkable, polymerizable, biodegradable composite formulation comprising poly(propylene fumarate) (PPF), bis(2,4,6-trimethylbenzoyl) phenylphosphine oxide (BAPO), and a alkyl fumarate, wherein said poly(propylene fumarate) and said alkyl fumarate are each present in an amount effective to produce a polymeric network useful for in vivo applications when said composite formulation is crosslinked.

2. The composite formulation according to claim 1 wherein said alkyl fumarate is a alkyl fumarate in which said PPF is soluble.

3. The composite formulation according to claim 1 wherein said alkyl fumarate is diethyl fumarate.

4. The composite formulation according to claim 1 wherein the mixture prior to crosslinking has a viscosity of 2 Pa s to 100 Pa s.

5. The composite formulation according to claim 1 wherein the mixture prior to crosslinking has a viscosity of 2 Pa s to 10 Pa s.

6. A process for forming a polymer network, comprising:
   providing an injectable, in situ photo-crosslinkable, polymerizable, biodegradable composite formulation comprising poly(propylene-fumarate) (PPF), a alkyl fumarate and bis(2,4,6-trimethylbenzoyl) phenylphosphine oxide (BAPO), wherein said poly(propylene fumarate) and said alkyl fumarate are each present in an amount effective to produce a polymeric network useful for in vivo applications when said composite formulation is crosslinked; and
   photo-crosslinking the poly(propylene fumarate) and fumarate derivative.

7. The method according to claim 6 wherein the crosslinking is accomplished by exposing the composite formulation to UV light.

8. The process according to claim 6 wherein said fumarate derivative is a fumarate derivative in which said PPF is soluble.

9. The process according to claim 6 wherein the injectable composite formulation prior to crosslinking has a viscosity of 2 Pa s to 100 Pa s.

10. The process according to claim 6 wherein the injectable composite formulation prior to crosslinking has a viscosity of 2 Pa s to 10 Pa s.

* * * * *